United States Patent [19]

Browning

[11] 3,969,228

[45] July 13, 1976

[54] QUALITY CONTROL MONITOR

[76] Inventor: Gordon D. Browning, 19056 Stanton Ave., Castro Valley, Calif. 94546

[22] Filed: Dec. 30, 1974

[21] Appl. No.: 537,199

[52] U.S. Cl. .............................. 209/73; 209/81 R; 209/111.5; 324/61 R
[51] Int. Cl.² ........................................... B07C 5/08
[58] Field of Search ................ 209/111.5, 73, 81 R, 209/81 A, 111.8; 324/61 R, 61 P, 61 QS, 61 QL

[56] References Cited
UNITED STATES PATENTS

| | | | |
|---|---|---|---|
| 2,992,731 | 7/1961 | Edelman | 209/81 R |
| 3,376,503 | 4/1968 | Lundstrom | 324/61 R |
| 3,826,979 | 7/1974 | Steinmann | 324/61 P X |

Primary Examiner—Robert B. Reeves
Assistant Examiner—Joseph J. Rolla
Attorney, Agent, or Firm—Warren, Chickering & Grunewald

[57] ABSTRACT

Apparatus is provided for detecting the presence and condition of a plurality of objects, such as liquid-filled bottles, cans, or other containers mounted within a sealed case for detecting broken or missing containers, leakage, and the like.

21 Claims, 6 Drawing Figures

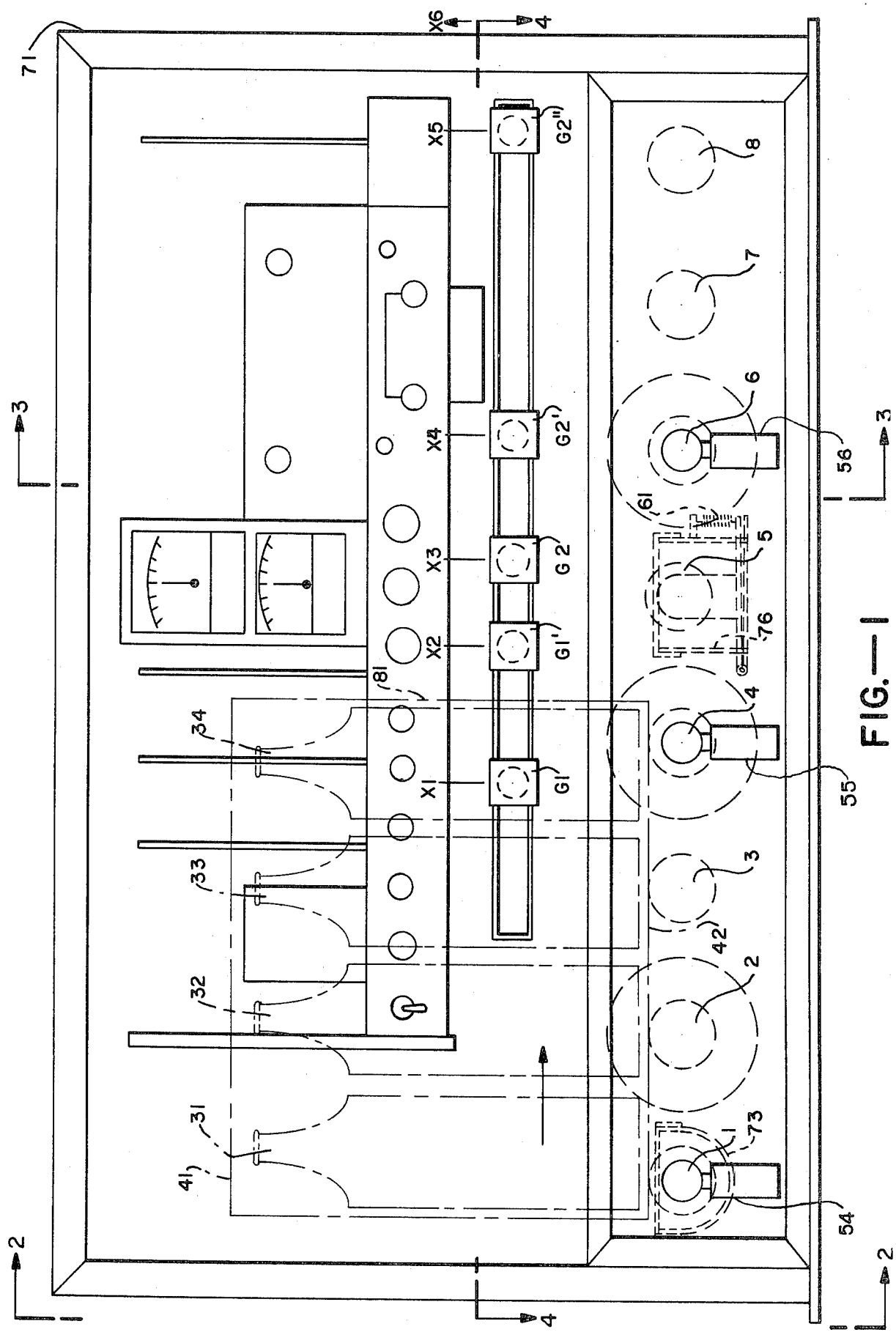
FIG.—1

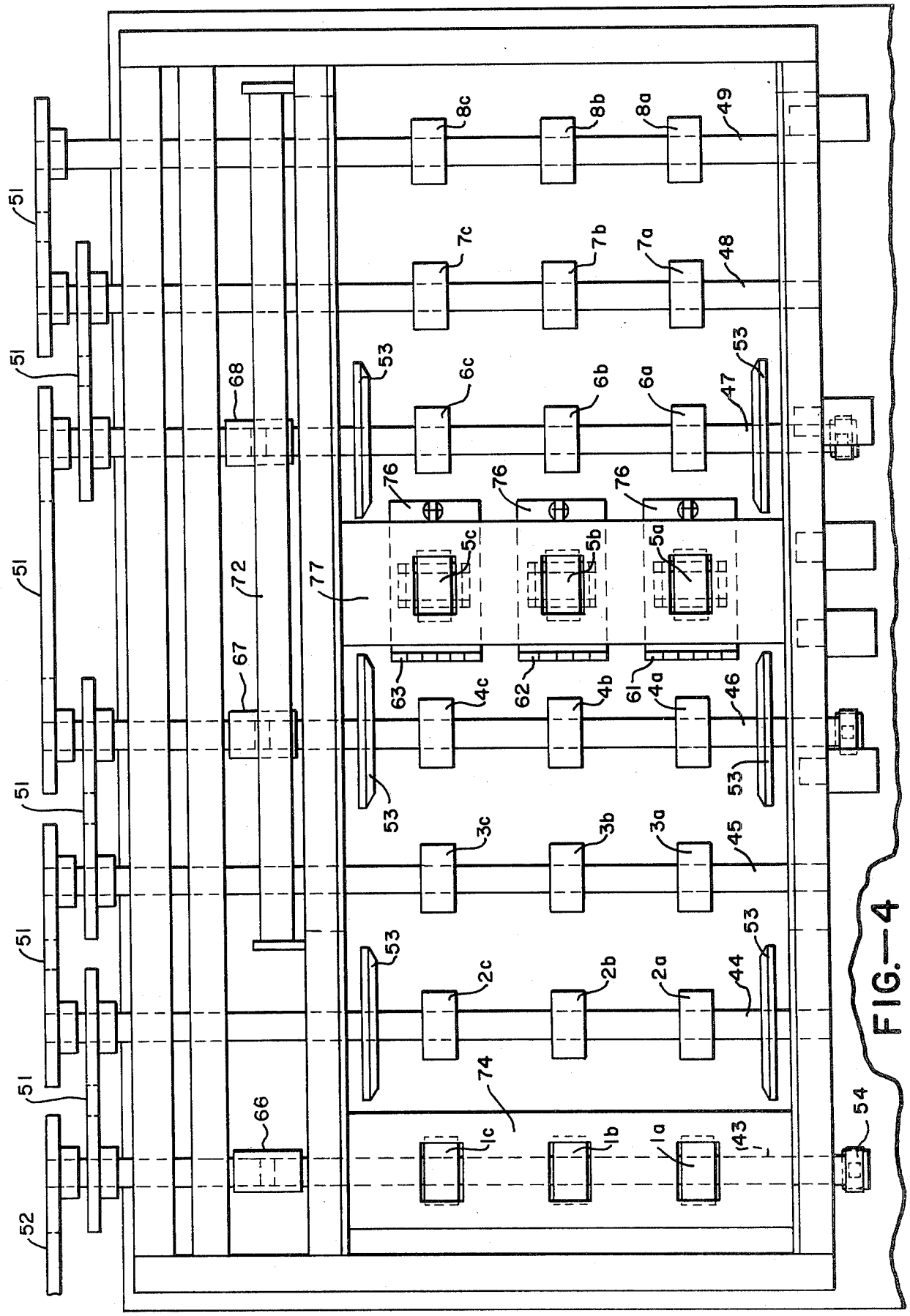
FIG.—4

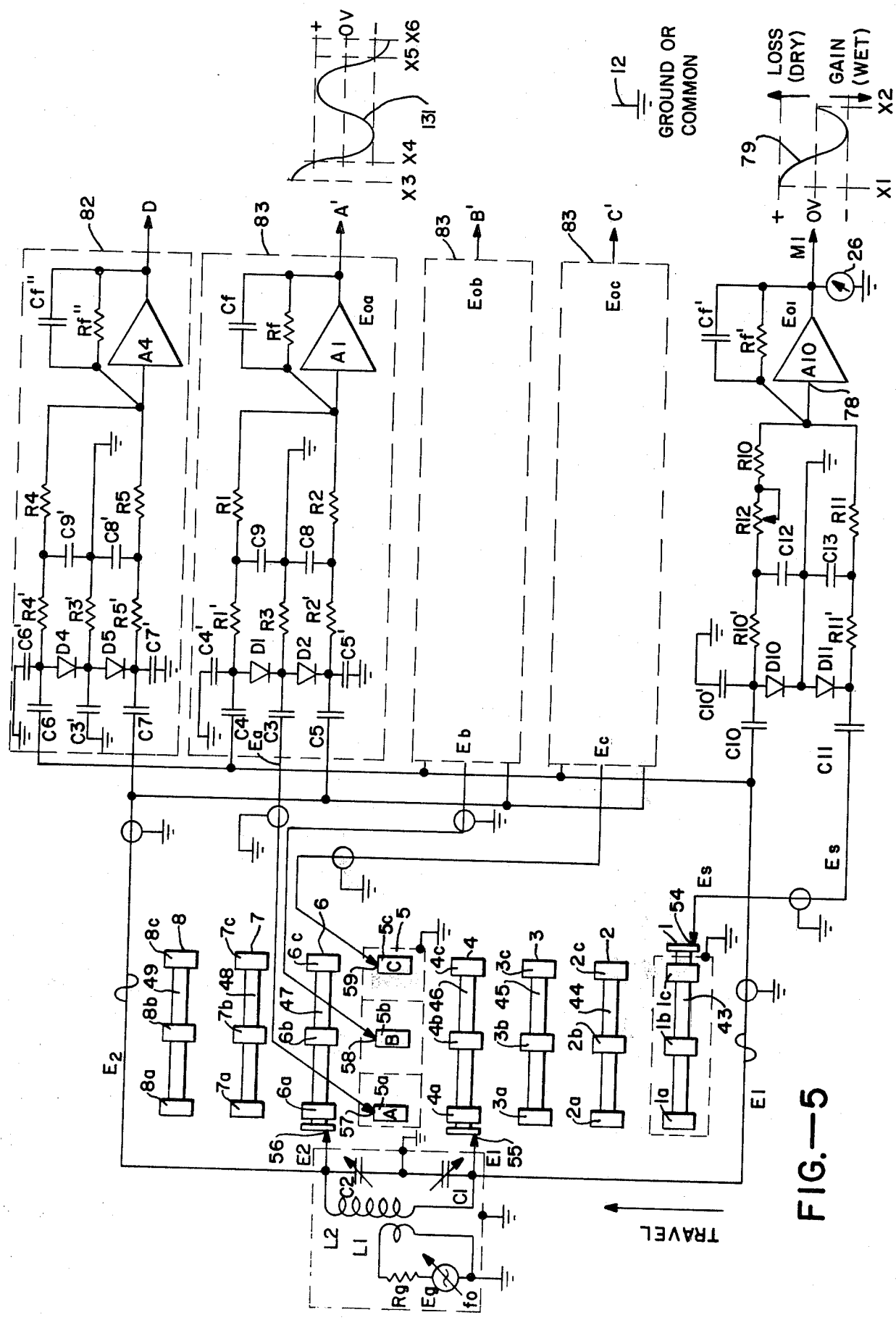
FIG.—5

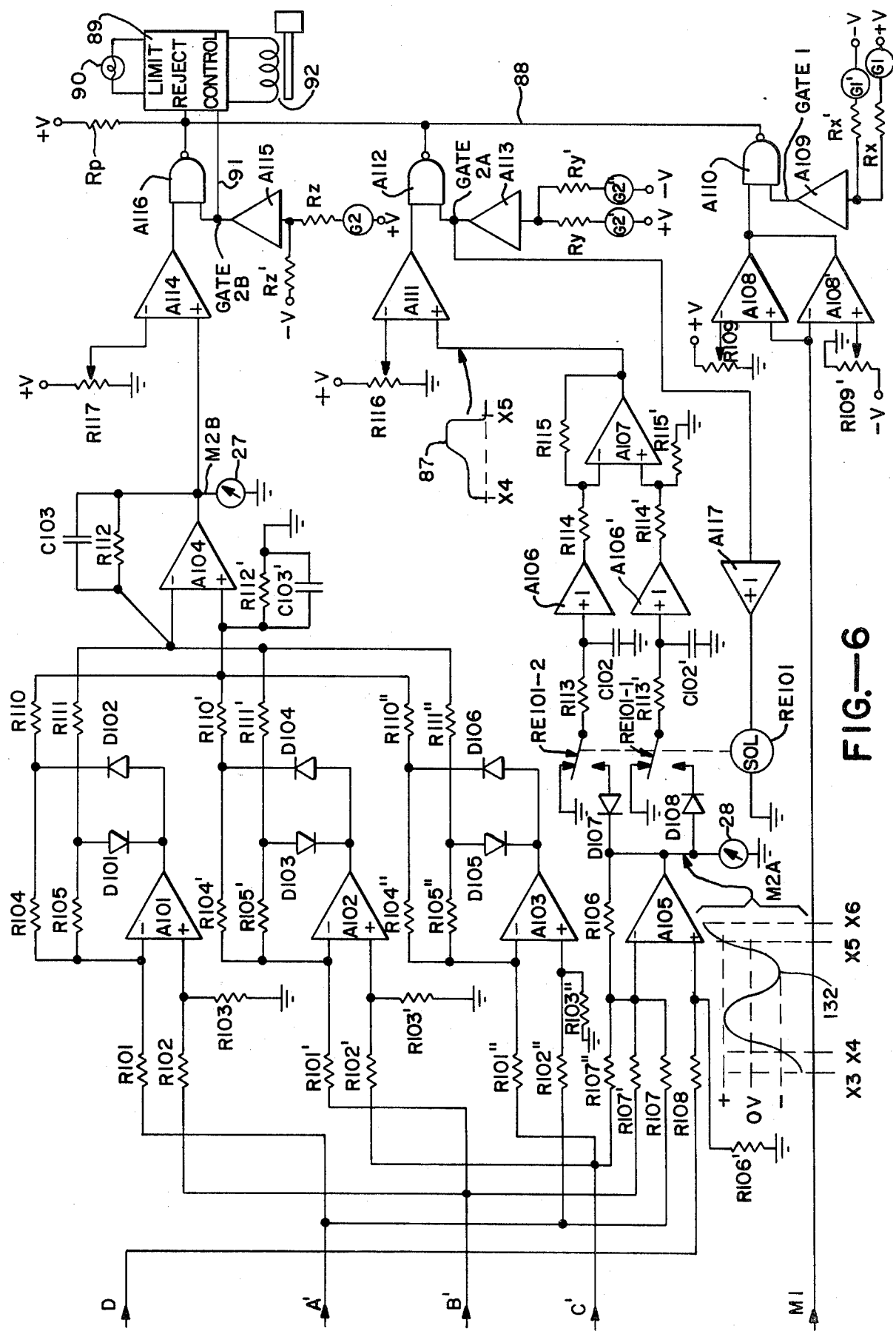
FIG.—6

QUALITY CONTROL MONITOR

BACKGROUND OF THE INVENTION

1. Field of Invention

The invention relates particularly to apparatus used in the final packaging stages of food and beverage processing plants wherein a plurality of liquid-filled containers are enclosed within cardboard cases and the like for storage, shipment, and sale; and to such apparatus as may monitor the cases for full weight and integrity of contents.

2. Description of Prior Art

Containers of the character described are subjected to some stress and shock in their handling and movement through the several machines for automatically filling and closing the containers and depositing them in shipping cases. Glass and plastic containers are subject to breakage or cracking, resulting in spillage of their content into the case. Leakage cannot only damage the case in which the defective container is mounted but may also penetrate adjacent cases. Particularly troublesome are containers which develop minute cracks which secrete the contents slowly and the resulting loss and imperfect contents can be seen only after passage of considerable time. In other instances, cases prior to loading may have been subject to moisture or high humidity atmosphere which may impair their strength. Another problem results when the apparatus for mounting the containers in the case fails to operate properly with the result that the case is passed through the line with one or more missing containers.

SUMMARY OF INVENTION

The apparatus of the present invention functions to provide several critical case sensing operations. Advantage is taken of the usual array of the containers in substantially even spaced columns and rows within the case. Energy transmission and receiving means is used to monitor different case areas opposite individual containers and to provide a rejection signal when there is a lack of similarity and when the dissimilarity reaches a predetermined amount. This type of monitoring is effective for detecting missing containers or instances where there has been an isolated small spot leakage within the container. In addition, a second monitoring is effected of the case bottom for sensing instances of gross spillage where a more or less uniform distribution of the contents may have occurred over the bottom of the case.

It is accordingly an object of the present invention to provide apparatus of the character described which will effectively monitor closed cases or broken or missing containers and for leakage occurring within the case or which may result from leakage in an adjacent case or simply from excessive moisture whatever the cause.

Another object of the present invention is to provide monitoring apparatus of the character above which will perform its several sensing operations rapidly and within the time frame permitted for cases moving on conveyers in the final packaging stages.

A further object of the present invention is to provide apparatus of the character above which will monitor cases containing a wide variety of contents, such as wines, brandy, beer, soups, sauces, salad dressings, medicines, vegetable and petroleum oils, and the like. In brief, the apparatus using the preferred embodiment as illustrated herein may be used for monitoring cases having containers of any liquid having a dielectric constant substantially greater than air.

The invention possesses other objects and features of advantage, some of which of the foregoing will be set forth in the following description of the preferred form of the invention which is illustrated in the drawings accompanying and forming part of this specification. It is to be understood, however, that variations in the showing made by the said drawings and description may be adopted within the scope of the invention as set forth in the Claims.

BRIEF DESCRIPTION OF DRAWINGS

FIG. 1 is a front elevation of a Quality Control Monitor constructed in accordance with the present invention.

FIG. 4 is a plan sectional view of the apparatus taken substantially on the plane of line 4—4 of FIG. 1.

FIG. 5 is a schematic diagram of a portion of the electronic circucit used in the preferred embodiment of the invention.

FIG. 6 is a schematic diagram of an additional portion of the electronic circuit.

DETAILED DESCRIPTION OF INVENTION

Figure 3:
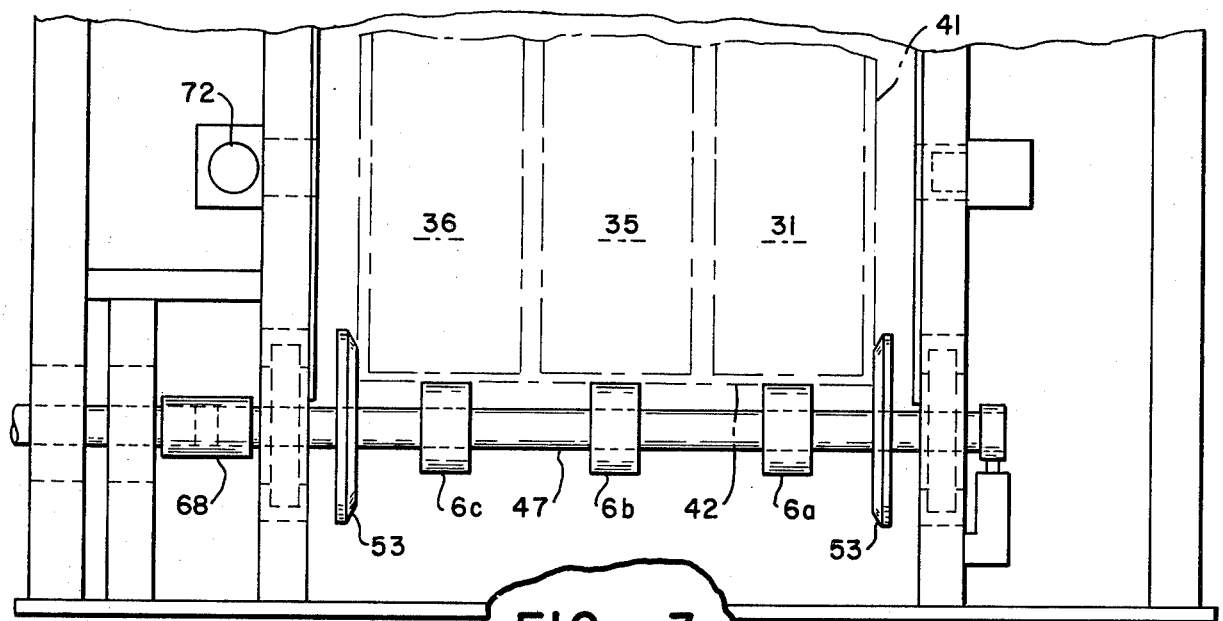
FIG. 3 is a cross-sectional view of the apparatus taken substantially on the plane of line 3—3 of FIG. 1.

The quality control monitoring apparatus of the present invention is adapted for detecting a plurality of objects, see containers 31, 32, 33, and 34, arrayed in a line or column in FIG. 1, and 31, 35, and 36, arrayed in a perpendicular row in FIG. 3, the containers being positioned within a case 41 in a three by four arrangement, making up a customary twelve containers to the case. The monitoring means of the present invention comprises means mounted exteriorly of the case and, more particularly, the bottom wall 42 thereof for transmitting energy to the wall wherein the type of energy selected and wall provide for transmission of energy through the wall to objcts 31–36, and the energy in objects providing for a return energy transmission through wall 42; means receiving the return energy from a plurality of wall areas, each being associated with one of the objects 31–36; and comparator means connected to the receiving means and comparing energy quantities received from the wall areas and being responsive to a predetermined dissimilarity of received energy quantities to provide a rejection signal. As another feature of the present invention, means is further provided for sensing energy transmission through wall 42 between spaced points thereon, and a further comparator is used to compare the latter energy transmission with a standard and to provide an output or rejection signal when the energy transmission deviates from the standard by a predetermined amount. More particularly, where the containers are arranged in rows and columns as here depicted, the comparator is constructed to provide a comparative matrix signal configuration, i.e., row to row and column to column.

Various forms of energy may be adapted for use in carrying out the comparative measuring technique of this invention, such as ultrasonic, infrared, laser, radioactive isotope (scattering), various conductance or inductive (or eddy loss) transmissions as well as dielectric or capacitance transmission or loss using AC, RF, or microwave applications. The preferred form of the invention, as illustrated herein, uses a dielectric technique involving displacement current resulting from an applied electric field and due to the capacitance of the case wall and objects where the latter are usually considered as dielectric or insulative; and the preferred applied field is an alternating RF voltage having a frequnecy sometimes referred to herein as Fo.

The apparatus may be designed to function while a case is at rest or while in motion, as for example, on a conveyer line in a packaging plant. In order to accomplish the monitoring function while the cases are in motion, the present apparatus is designed for mounting in contiguous relation to a conveyer line and embodies a series of rollers 1, 2, 3, 4, 5, 6, 7, and 8, see FIG. 1, which are mounted for supporting the bottom wall 42 of the cases as they pass the apparatus. These rollers are preferably mounted for rotation about parallel axes and are spaced apart by substantially the spacing of the rows of containers as depicted by containers 31–34 in FIG. 1 so that at one point in time each of the several rows will overlie one of the rollers. Moreover, certain of the rollers are driven so as to drive the case through the monitoring apparatus at conveyer speed, and certain of the rollers are connected to the energy transmitting and receiving means as above noted.

As another feature of the present construction, each of the rollers 1–8 and especially rollers 1, 4, 5, and 6 are formed as three separate roller sections, see FIG. 4, so that the rollers will not only underlie the several rows of containers, FIG. 1, but will also underlie the several columns of containers, FIG. 3. Accordingly, three separate roller sections 1A, 1B, and 1C are mounted for coaxial rotation on a common shaft 43; and similarly separate roller sections 2A, 2B, and 2C are mounted on common shaft 44; roller sections 3A, 3B, and 3C are mounted on common shaft 45; roller sections 4A, 4B, and 4C are mounted on common shaft 46; roller sections 6A, 6B, and 6C are mounted on common shaft 47; roller sections 7A, 7B, and 7C are mounted on common shaft 48; and roller sections 8A, 8B, and 8C are mounted on common shaft 49. Shafts 43–49 are coupled by pulley and belt drives 51 for joint rotation in a common direction driving cases from left to right as seen in FIGS. 1 and 4, with a motor driven pulley and belt drive 52 here shown connected to shaft 43. Additionally, and with reference to FIGS. 2, 3, and 4, it will be noted that guide discs 53 are here mounted on shafts 44, 46, and 47 for restricting case movement longitudinally of the shafts and holding the case for centralized movement through the apparatus with the columns of containers in each case maintained in alignment with the roller sections. Roller sections 5A, 5B, and 5C are not driven in the present structure but are separately mounted for independent but coaxial rotation as idlers. Preferably, the roller sections are adjustably secured to their respective shafts to permit customized alignment with various cases which may be run through the apparatus.

Roller sets 1, 4, 5, and 6 are here used for the transmission and receipt of energy as above noted, while roller sets 2, 3, 7, and 8 are not electrically or otherwise used in the monitoring operation, and hence are preferably formed of plastic or other heat/electrical insulation composition to thereby keep them out of the probing circuit. Electrical conduction to roller sections 1A, 1B, and 1C may be effected by a brush and slip ring connection 54 to shaft 43, and similarly electrical connection to roller sections 4A, 4B, and 4C may be effected by brush and slip ring connection 55; and electrical connection to roller sections 6A, 6B, and 6C may be effected by bruish and slip ring connection 56 connected to shaft 47. Individual brush and slip ring connections 57, 58, and 59 are made to roller sections 5A, 5B, and 5C, respectively, which are schematically illustrated in FIG. 5. Each of the electrified roller sections 1A, 1B, and 1C, 4A, 4B, and 4C, 5A, 5B, and 5C, and 6A, 6B, and 6C are preferably formed with metallic hubs mounted on metallic shafts for conducting electricity and surrounded by a peripheral layer of electrical insulation material making dielectric contact with the bottoms of the cases. Rollers 5A, 5B, and 5C are mounted electrically insulated from ground and each other; and, moreover, and as will be seen from FIGS. 1 and 4, these roller sections are provided with spring-loaded mounts 61, 62, and 63 for elevating the individual rollers with small tension slightly above the plane of roller sets 1, 4, and 6. The weight of cases passing over rollers 5A, 5B, and 5C will depress them into planar position with respect to the other rollers and ensure good dielectric contact of roller set 5 with the traveling case bottom. Preferably all of the rollers except set 5 are mounted on shafts journalled in insulative bearing structures, such as a plastic Nylon block, so that the probing rollers are fully insulated to ground and from each other. They are also preferably insulated from their rotative drive sources by insulation shaft couplers 66, 67, and 68, see FIGS. 3 and 4.

Figure 2:
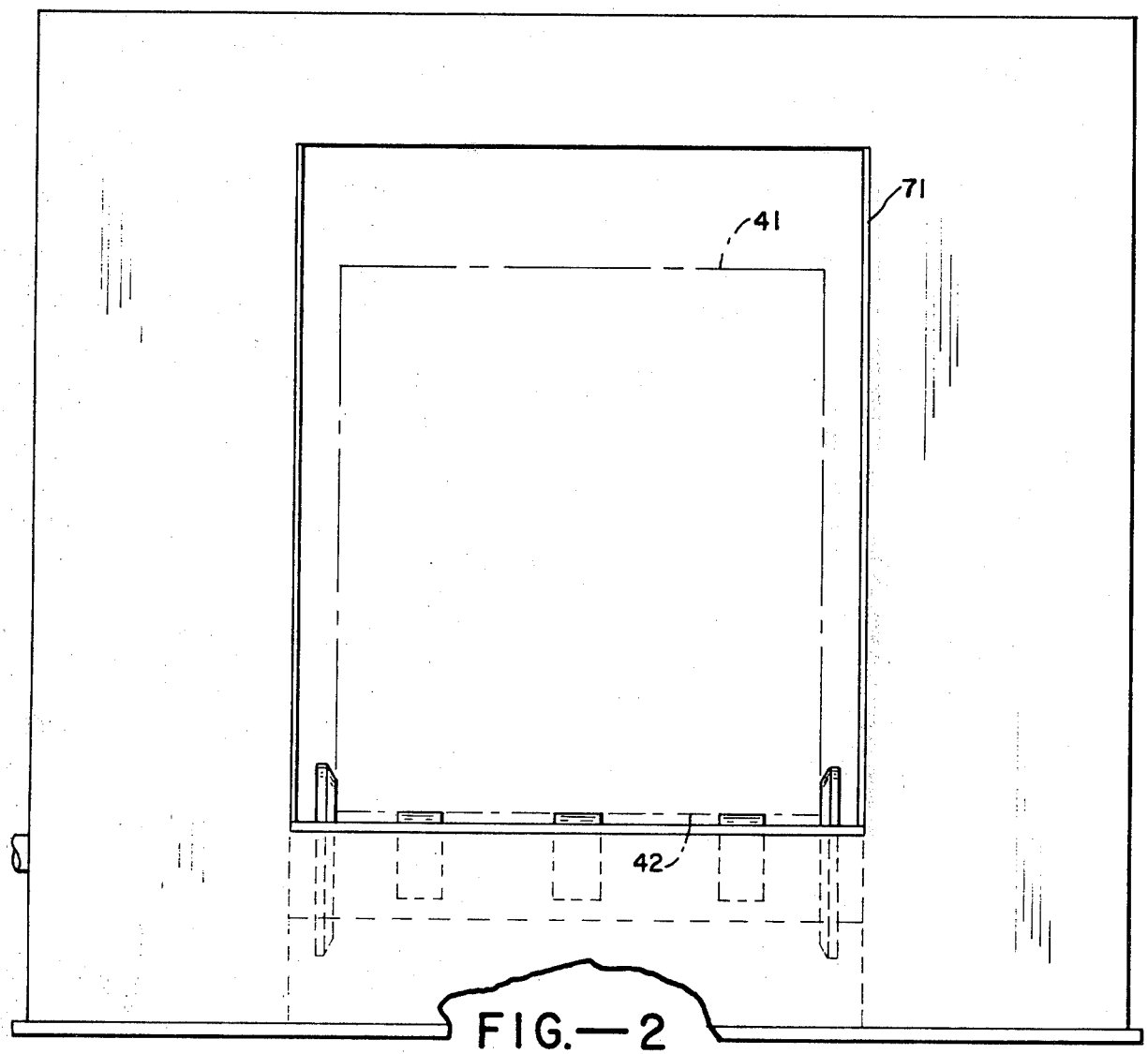
FIG. 2 is an end elevation of the apparatus.

Preferably, the several shafts and rollers are mounted and assembled within a housing 71 providing a complete tunnel enclosure for case 41 as it moves through the apparatus during the several monitoring operations, see FIGS. 1, 2, and 3, the surrounding walls of the housing being preferably conductive and grounded to provide RF shielding for the apparatus.

Additional sensing or gating means is provided for selectively energizing various portions of the electronic circuit at various positions of the case as it moves through the unit. Such means here comprises an elongated light 72 mounted on one side of the tunnel, see FIGS. 3 and 4, and a plurality of photoelectric cells G1, G1', G2, G2', and G2'' mounted at the opposite side of the tunnel at substantially the same elevation as and facing lamp 72 which may conveniently comprise a fluorescent tube. Both the lamp and photoelectric cells are mounted at an elevation where the light from lamp 72 to the cells will be intercepted by case 41 traveling through the apparatus, as from left to right as seen in FIGS. 1 and 4. The traveling case breaks the light path causing logic switching to take place as more fully hereinafter developed. Photocell G1 is mounted just ahead of roller set 4, and G1' is mounted just ahead of roller set 5. These positions are designated X1 and X2 in FIG. 1. The travel of the case between X1 and X2 is herein referred to as gate 1. Gate 2 interval is defined by the gate travel for the entire length of case 41 blocking the light for photoelectric cell G2 at point X3. Between points X4 and X5 a coincident gate 2A is generated where the case 41 is traveling across the light paths for photoelectric cells G2' and G2'' providing an enable signal for a measurement sometimes referred to herein as 2A only between X4 and X5. Gate 2B terminates when the leading edge of case 41 arrives at position X6.

The overall sensing scheme used in the preferred form of the invention is illustrated in FIG. 5. As hereinabove noted, the present invention makes at least two basic measurements, viz, a determination of resultant electrical capacitance change (for dielectric coefficient change) due to the change in mass and/or liquid over a substantially entire wall area, such as the bottom wall of the case; and the change in capacitance associated with incremental areas, i.e., area to area comparison. Of importance in carrying out the present invention for various applications is the size and shape and frequency of the applied AC field and the measuring probes coupling, shielding, and loading impedance. Where RF energy is used as in the present case, shielding of at least certain of the rollers is helpful. Accordingly, as will be noted from FIGS. 1 and 4, a segmental cylindrical shield 73 is mounted under roller assembly 1 and is capped by a cover plate 74 having cutouts exposing only the top peripheral portions of rollers 1A, 1B, and 1C. Rollers 5A, 5B, and 5C are mounted within individual shielded boxes 76 capped by a common cover plate 77 which is again provided with cutout portions or windows for exposing only the top peripheral portions of rollers 5A, 5B, and 5C.

With reference to FIG. 5, the RF potential used by the present embodiment is generated at oscillator or generator E$g$ which with its internal resistance R$g$ is connected to the primary L1 of an RF transformer having its secondary L2 connected to roller sets 4 and 6 by brush and slip ring connections 55 and 56. Where RF energy is used, some form of capacitive coupling could be substituted for the conductive brush and slip ring connection. Preferably, secondary winding L2 is tuned and capacitance balanced by capacitors C1 and C2 so that the resulting probing voltages E1 and E2 applied to roller sets 4 and 6 are substantially equal. This can be adjusted by making capacitors C1 and C2 variable, and their capacitance can be made high compared to the stray roller capacitance to ground with or without a case 41 present. Preferably, the secondary circuit is structured to resonate at a frequency F$o$ of about 3 mHz. The circuit illustrated is, of course, but one example of a common oscillator which can be capacitively coupled in series with each capacitance C1 and C2 in such a way as to form a push-pull oscillator configuration. In this way, L2, C1 and C2 determine F$o$ along with the stray capacitance caused by case 41 and rollers 4 and 6. The amplitude of E1 and E2 is preferably set fairly high in the order of 600 to 1,200 volts peak to peak and is preferably adjustable by adjusting the amplitude of the output of E$g$ as illustrated. Optionally, E$g$ may be turned on and off to synchronize with the required gating of the probing circuits.

The first monitoring occurs as case 41 spans rollers 1 and 4. During this time, potential E1 is supplied to roller 4 and is capacitance coupled by case 41 to roller 1 which produces an output voltage E$s$ which affords an analog signal proportional to the overall mass or flooding of case bottom 42. Preferably, rollers 1 and 4 are spaced to span at least 80–90% of the length of the case bottom. A receiver or detector circuit is connected to E$s$ as illustrated in FIG. 5 where the input voltage E$s$ is applied to capacitor C11 which develops a positive to ground voltage across diode D11 which, in turn, produces a plus summing current through R11' and R11 at the inverting input 78 of amplifier A10. In like manner, the input voltage E$s$ is applied to capacitance divider C10 and C10' to ground and produces an opposite negative DC voltage across diode D10 resulting in a minus current through R10', R12, R10, and to the input 78. Both R10', C12 and R11', C13 provide R-C RF bypassing networks for respective sides of the circuit. With a standard case 41 placed across rollers 1 and 4, R12 is adjusted for a null or zero at M1 output voltage E$ol$ monitored with the aid of meter 26. When properly set, a fairly equal swing in loss (dry) to gain (wet) signal is produced as the case travels between X1 and X2 and as illustrated by wave form 79, see FIG. 5. This swing in E$ol$ represents a typical case. The sensitivity of this circuit is set by feedback resistance R$f'$ along with integration capacitor C$f'$. C$f'$ is made large enough to bypass a small amount of roller contact noise, typically a period of 1 millisecond or less, and does not restrict the gain band width which is effectively set by R$f'$. In practice, the sensitivity of this circuit provides a high output when any given row of containers is missing which produces a positive offset in E$ol$, or typically a 20–100% evenly distributed contents flooding of case bottom 42.

As the leading edge 81 of the case moves forwardly, see FIG. 1, and onto roller set 5, gate 2 comes on, and the second measurement begins. Roller sets 4, 5, and 6 are used for probing where a balanced field along the case bottom path is provided between roller sets 4 to 6 by oppositely phased voltages E1 and E2. Each roller in set 5 provides an output capacitively divided between E1 and E2, resulting in voltages E$a$, E$b$, and E$c$ as separately channeled null outputs. E$a$, E$b$, and E$c$ will be identical under good case conditions. However, when viewing the case on the basis of a row to row arrangement of the containers, the outputs from rollers 5 will be high at the beginning of gate 2, at X3, where case 41 generally bridges rollers 4 and 5; and in a similar fashion higher gain will again appear when roller sets 5 and 6 are energized by the oppositely phased voltage E2. The interval of case travel is considered the overall measuring interval of measurement 2 or specifically 2B where output E$a$ and E$b$ and E$c$ are all compared with each other, resulting in a column to column comparison of E$a$, E$b$, and E$c$.

Conversely, the interval between X4 and X5 intermediate and simultaneous G2' is then switched on enabling the interval of measurement 2A, or row to row comparison where all three channels, E$a$, E$b$, and E$c$, should be close to zero under good case conditions. As shown in FIG. 5, all detector circuits are identical, and the explanation of one will serve for all. E$a$ is preferably connected by shielded line to coupling capacitor C3, thereby producing its signal at the junction of diodes D1 and D2 and across resistor R3 to ground. The value of resistor R3 is small compared to loading resistance on the opposite sides of each of the signal diodes D1 and D2 where E1 is applied across capacitance divider C4 and C4' to ground, producing a negative to ground voltage drop across diode D1 and a minus current through series summing resistances R1' and R1 connected to the input of inverting summing amplifier A1. In like manner, voltage E2 is applied across capacitance divider C5 and C5' to ground producing a positive voltage across diode D2 and a plus current through series resistors R2' and R2 into the input of amplifier A1. Voltage E1, as above noted, is divided equally with respect to voltage E2 by their respective capacitor dividers to provide appropriate operating voltage levels for each diode. Also, resistor R1', capacitor C9, resistor R2' and cappacitor C8 act as RF bypass networks for the respective sides. With E$a$ equal to zero, at null, no voltage is added to either diode D1 or D2, and the overall circuit is essentially at null where the resultant inverting amplifier A1 output E$oa$ is essentially zero. A typical output voltage E*oa* wave form 131 is shown in FIG. 5 at point A' for various travel positions of case 41 during the overall interval of gate 2. When E*a* is offset, it will be phased towards either voltage E1 or E2, reducing the respective diode voltage thereby driving the amplifier more positive or more negative depending on the phase and amplitude of E*a*. Since E*a*, like E*b* and E*c*, is derived from a mainly capacitive voltage divider, sharp phase reversal is obtained between an offset towards E1 or E2. Although the circuit can act as a phase detector, it acts much more as an amplitude base null or offset detector due to its high capacitive coupling to E*a* from E1 and E2 as established by the case and probing system described.

As above noted, voltages E1 and E2 should be essentially equal, typically within about 10% or better. The balanced high capacitance resonated tank circuit feeding rollers 4 and 6 can maintain this relationship fairly well. However, if E1 goes up, E2 will decrease, or vice versa, and, in turn, this change can produce a significant steady state offset of mid voltage points E*a*, E*b*, and E*c* at roller 5. The derived output of measurement 1, E*ol*, in practice is not affected by variations in these voltages since the measurement 1 detector circuit compares differentially E*s* with E1, where both will vary proportionately. Little effect is created in measuring the resultant transfer through case 41 over the usual variation in range of E1. To compensate for an imbalance of voltages E1 and E2, a detection circuit 82 basically identical to the column detector 83 is used just to sense voltages E1 and E2. In detector 82, diode junction D4 and D5 is bypassed by capacitor C3' to ground across resistor R3' having a value the same as R3. Analogously, voltage E1 is applied across capacitance voltage divider C6 and C6' to produce a negative to ground DC voltage drop across D4 producing a minus current into summing resistances R4' and R4. Opposite voltage E2 is applied across capacitance voltage divider C7 and C7' to produce a positive to ground DC voltage across the diode D5 and a plus current through series summing resistors R5' and R5 into the input of summing amplifier A4. Resistors R4' and R5' and capacitors C9' and C8' provide RF bypassing, and capacitor C*f''* rolls-off the band width of amplifier A4 to suit the signal to noise considerations. Resistor R*f''* can be fixed or adjustable and sets the DC gain of amplifier A4 as required. This circuit's coefficient of output voltage drift against temperature and/or common voltage changes will track closely that of its neighboring detectors. The resulting E1 - E2 compensation output at D, the output of amplifier A4, is used as a comparison signal for row to row comparison measurement 2A, where E*oa*, E*ob*, and E*oc* are all summed together and compared to this output voltage at D. Also, as an option, this output can be used as a signal for an automatic tuning system equivalently adjusting capacitors C1 or C2, thereby keeping voltages E1 and E2 balanced as required. Effecting a consistent demodulation sensitivity of voltages E*a*, E*b*, and E*c* by avoiding a large voltage unbalance of the column detector's signal diodes D1 and D2 is important for both measurements 2A and 2B.

The electronic circuit depicted in FIG. 6 shows in somewhat simplified form the final derivation of measurements 1 and 2, along with the limit comparison limit error rejection enabling an overall rejection scheme. Measurement 1 voltage E*ol*, FIG. 5, is fed directly to an M1 limit input window comparator comprising amplifiers 108 and 108'. It is helpful to monitor this voltage by the use of a zero centered voltmeter 26, shown in FIG. 5, when setting the limits. As above noted, case 41 causes photocell G1 to cut off, and the output of photocell amplifier 109 goes positive producing a logical 1 at the input of NAND gate A110. If a predetermined positive or negative limit is exceeded from measurement M1, E*ol*, and then amplifiers 108 or 108' changes from a logic zero to 1 and a rejection trigger is initiated. To set the limits, a case may be slowly brought through the apparatus with at least one row of containers missing and then again with added mass or a generally flooded bottom and the respective limit adjustments made to suit each condition.

In effecting the next measurement M2B, it is also helpful to monitor the operation by a DC voltmeter 27 connected at the output of amplifier 104. Amplifiers A101, A102, and A103 make up the column comparators where the output of each amplifier is diode directed to provide separate positive outputs by steering diodes D102, D104, D106, and D101, D103, and D105, respectively, for the negative outputs. Amplifier A101 provides the algebraic sum of voltages E*oa* and E*ob*. Amplifier A102 provides the algebraic sum of voltages E*ob* and E*oc*. Finally, for three columns as here illustrated, amplifier A103 provides the algebraic sum of voltages E*oc* and E*oa*. Each individual amplifier A101, A102, and A103 has its derived positive diode output connected to an identical summing input resistor R110, R110', and R110'', respectively; and applied to the plus input of balanced summing amplifier A*a*104. The negative outputs of amplifiers A101, A102, and A103 are similarly connected to identical summing resistors R111, R111', and R111'', respectively, which are connected to the minus input of amplifier A104. Feedback resistor R112 along with balancing resistor R112° set the DC gain of this amplifier where some band width roll-off is provided by capacitor C103 and capacitor C103' as required for amplifier-diode switching, noise, typically less than 100 microsecond transients. Feedback resistors R104, R105, along with balancing resistor R103, set the gain of column amplifier A101. Resistors R104', R105', and R103' are similarly connected to amplifier A102; and resistors R$\psi$'', R105'', and R103'' are similarly connected to amplifier 103. Associated summing resistors are connected to associated amplifier inputs where point A' is at resistor 101, B' is at 101'', and C' is at 101'''.

The foregoing connections make a closed delta circuit configuration which is one view of this three-channel example. It will be noted that the number of amplifiers are equal to the number of channels: The scheme may also be referred to as a matrix comparator. Ideally, the output of amplifier A104, measurement M2B, is always zero, i.e., at null, while a good case 41 travels through the apparatus during the G2 interval that is between positions X3 and X6. In practice, a small amount of error ripple is present. Also, any input offsets will drive amplifier A104 output only positive. This output, monitored by meter 27, is limit compared by amplifier A114 with a limit preset by the plus limit set potentiometer R117 which is preset to trip on a sample case that has any one of its containers missing or any container area soiled or moistened as required. Upon reaching a limit, the output of amplifier A114 will swing to a logical 1 while the output of photocell amplifier A115 is at a logical 1 (during interval G2) and NAND gate A116 goes to zero to provide a rejection trigger due to the measurement M2B limit.

Measurement 2A is derived at the output of balanced summing amplifier A105. The derived column signals are all summed together into the negative input of amplifier A105 where line A', voltage Eoa, is connected to resistor R107, line B', voltage Eob, is connected to resistor R107', and line C', voltage Eoc, is connected to resistor R107''. These summed voltages to the negative side of A105 are compared with that produced through resistor R108 voltage from the previously described E1 - E2 compensation output, line D, FIG. 5. The gain of amplifier A105 is set by resistor 106 and balancing resistor R106'. In this instance, also, it is helpful to monitor the output by the use of a DC voltmeter 28 for measurement 2A. The wave form 132 for this measurement is the same as voltages Eoa, Eob, and Eoc except inverted, see wave form 131, FIG. 5. It may be noted that this derivation of measurement 2A can be also obtained by connecting all individual rollers in set 5 together and detecting their output with just one detector amplifier circuit as shown in FIG. 5. As noted above, it is necessary with this arrangement to allow the limit rejection only during coincidental gate 2A (with that of gate 2B) so that the offset caused by case 41 not being in contact over all three roller sets 4, 5, and 6, does not create a false limit rejection. This out-of-limit prevalent voltage exclusion can be seen in FIG. 5 by the output voltage, measured to ground 12, as typified by wave form 131, at lines A', B', and C' between intervals X3 to X4, and X5 to X6 where, during interval gate 2A, each channel voltage is normally within limits between X4 to X6. It has been found that to effect the highest signal to noise ratio with the normally positive and negative going row to row wave form 132, as derived at the output of amplifier A105, a peak to peak measurement of its limit determination be made since a steady state base line has been difficult to achieve in practice. To satisfy this requirement, a sample and hold positive and negative detector is here used. To simplify illustration, sampling and holding capacitors C102 and C102' are switched by a double pole, double throw relay RE101 which is energized by the output of buffer-driver amplifier A117 when photocell amplifier A113 output is at logical 1 during gate 2A interval. This switching can also be done with a solid state circuit. During this time, any negative peaks are rectified by diode D107 to charge capacitor C102 negative through relay RE101-2 normally open contacts and series current limit resistor R113 while any positive peaks are rectified by diode D108 through relay RE101-1 contacts and series current limit resistor R113' to charge capacitor C102' positive. Both capacitors charge close to the value of the peak output voltage of amplifier A105. Amplifiers A106 and A106' are voltage followers providing a load isolation for capacitors C102 and C102', respectively. Amplifier A106 drives the negative input of balanced summing amplifier A107 negative through summing resistor R114, while amplifier A106' drives the positive summed input through resistor R114' positive. This results in positive only going output from amplifier A107. Feedback resistor R115 along with balancing resistor R115' set the gain of amplifier A107. The output wave form 87 of amplifier A107 takes a step-like shape where the following sequential peak is added to the previous peak, and the output from amplifier A107 then is representative of the worst case (peak to peak) exclusion. The output of amplifier A107 is then compared by limit amplifier A111 with that preset by R116 plus limit potentiometer. In a similar manner to that above described, the output of amplifier A111 provides a logical 1 to the respective input of NAND gate A112 and since the output of amplifier A113 provides a logical 1, during this interval, at amplifier A112 second input, a logical zero reject signal is provided at the output of A112. To set the limit for measurement 2A, one or more containers may be removed from any row or, alternatively, soiling or moisture added to an otherwise normal case while resistor R116 is adjusted at proper limit while the case travels through the apparatus. After the end of gate 2A (output of amplifier A113 being at logical zero), relay RE101 is de-energized and both capacitors C102 and C102' are discharged through resistor R113, relay switch contacts RE101-2, and resistor R113', relay contacts RE101-1 to ground resetting this circuit for the next test.

The position of case 41, as seen in FIG. 1, is sensed by the use of identical photo-resistive type cells. The photocell amplifiers A109, A113, and A115, see FIG. 6, are all identical inverting type with summing resistors associated with their inputs as illustrated. All amplifiers are summing comparator type and are so biased for outputs to go from logical zero (zero volts) to a given plus sign + logical 1 with a more negative offset at their inputs. When light is blocked to G1 on gate 1, A109 output swings to + logical 1 due to the more minus current through resistor Rx' than plus current through resistor Rx. Next, the input is offset back positive when G1' is blocked (preset biasing at the input of A109) and an A109 output returns to zero. As the case goes through, G1 will turn on, then G1', while A109 still keeps reset at zero. The same operation holds true for A113 where its output swings to + logical 1, gate 2A when G2' (connected to resistor Ry) is blocked and zero again with G2'' blocked connected to Ry'. Like before, A113 stays at zero while G2'' and G2' both see light (turned on) in reversed order. Meanwhile, Gate 2B (overshadowing gate 2A) is turned on by the first resistor Rz' sourced directly from −V, as shown. During the whole case 41 length, G2 (connected to resistor Rz) is blocked and the output of A115 stays at + logical 1 and stays at zero while G2 is on.

The above-mentioned biasing voltages shown in FIG. 6 (+V and −V) are the standard operating voltages for this circuit, preferably each regulated 15 volts DC.

As shown in FIG. 6, the output of all NAND gates are connected together in a common line 88 in a wired OR configuration with a passive pull-up resistor Rp. The output at conductor 88 need only be a momentary logical zero "trigger" to constitute a rejection signal when case 41 is within the measuring area of the conveyer. Any appropriate reject control circuit 89 may be used. An integral register may also be used to switch on a pilot lamp 90 to indicate a limit being reached, after which gate 2B goes from logical 1 to logical zero, while case 41 leaves its position so as to constitute a clock trigger at input 91, activating the ejector 92 drive circuit. The rejection may make use of a simple time delay or a shift register drive so arranged that ejector 92 will push the defective case off from the conveyer line at a downstream rejection point.

What is claimed is:

1. Apparatus for detecting a plurality of objects mounted on or proximate to one side of a wall comprising:

means mounted at the opposite side of said wall and transmitting energy thereto;

said energy and wall providing for transmission of energy through said wall to said objects, and said energy and objects providing for return energy transmission through said wall;

means receiving said return energy from a plurality of wall areas, each of said areas being associated with one of said objects;

comparator means connected to said return energy receiving means and comparing energy quantities received from said areas;

means connected to said comparator means and responsive to a predetermined dissimilarity between said received energy quantities to provide a rejection signal;

means sensing energy transmission through said wall between spaced points thereon; and second comparator means connected to said energy transmission sensing means and comparing said energy transmission with a standard and providing an output signal when said energy transmission deviates from said standard by a predetermined amount.

2. Apparatus as defined in claim 1, said energy transmitting means comprising an electric generator; and said receiving means comprising an electric sensing means.

3. Apparatus as defined in claim 1 for detecting penetrant in the bottom of any of a succession of moving cases, said energy transmission sensing means comprising:

a pair of electrodes mounted for movement thereover of the case bottoms and being spaced to simultaneously engage each case bottom, said electrodes being formed to provide an electrically insulated contact with said case bottoms;

an RF generator connected to one of said electrodes and applying a first electrical potential thereto;

electric sensing means connected to the other electrode and deriving a second electrical potential therefrom; and said second comparator means comprising a circuit connected to said generator and said sensing means and responsive to a predetermined difference between said first and second potentials to provide a rejection signal.

4. Apparatus as defined in claim 3, said electrodes comprising a pair of rollers.

5. Apparatus as defined in claim 4, and a shield surrounding the uncontacted portion of said other electrode roller for restricting the electrical pickup to said case bottoms.

6. Apparatus as defined in claim 5, said comparator circuit comprising:

means rectifying said potentials to provide first and second DC voltages respectively and of opposite polarity; and an amplifier having an input connected to said rectifying means and functioning to sum the difference of said voltages.

7. Apparatus as defined in claim 6, and means for adjusting the amplitude of one of said voltages to null the output of said amplifier for a standard case, whereby said amplifier output and magnitude thereof will swing oppositely polarity-wise in response to variations in presence of said penetrant in amounts above and below a pre-selected standard; and means initiating said rejection signal when said output exceeds a prescribed deviance from said standard.

8. Apparatus as defined in claim 7, and means for adjusting said prescribed deviance.

9. Apparatus for detecting a plurality of objects arranged in columns and rows on or proximate to one side of a wall comprising:

means mounted at the opposite side of said wall and transmitting energy thereto;

said energy and wall providing for transmission of energy through said wall to said objects, and said energy and objects providing for return energy transmission through said wall;

means receiving said return energy from a plurality of wall areas, said wall areas being arranged in rows and columns conforming to said rows and columns of said objects, and each of said areas being associated with one of said objects;

comparator means connected to said return energy receiving means and comparing energy quantities received from said area rows and columns to provide a comparative matrix signal configuration; and means connected to said comparator means and responsive to a predetermined dissimilarity between said received energy quantities to provide a rejection signal.

10. Apparatus as defined in claim 9 wherein said objects are mounted on said wall in rows having a predetermined spacing;

a plurality of rollers mounted for supporting said wall and connected to said energy transmitting means, said rollers being mounted for rotation about parallel axes spaced apart by substantially the aforesaid spacing of said rows; and said rollers being subdivided into sections corresponding in number with and spaced to underlie said columns.

11. Apparatus as defined in claim 10, certain of said rollers being connected to said receiving means.

12. Apparatus as defined in claim 11, and means shielding the transmission of said energy between said transmitting and receiving rollers.

13. Apparatus as defined in claim 11, said transmitter connected rollers and said receiving means connected rollers being mounted to underlie alternate of said rows.

14. Apparatus as defined in claim 13, said roller sections being axially spaced to underlie the approximate centers of said columns and coaxially mounted for joint rotation on common shafts.

15. Apparatus for detecting the presence and condition of a plurality of containers mounted in substantially parallel rows in a succession of moving cases comprising;

at least three rollers mounted for movement thereover of the bottoms of said cases and being spaced to simultaneously engage each case bottom, said rollers being mounted for rotation about parallel axes spaced apart by substantially the spacing of said rows whereby said rollers will simultaneously substantially underlie the containers in three adjacent rows in each case, said rollers being formed to provide an electrically insulated contact with said case bottoms;

an RF generator connected to a first and third of said rollers positioned on opposite sides of an intermediate second roller, said generator applying out-ofphase RF potential to said first and third rollers; and an RF receiver connected to said second roller and providing an output as a function of the differences in dielectric coefficients extant in the RF paths through said case and objects therein between said first and third rollers and said second roller and providing a rejection signal when said output exceeds a prescribed standard.

16. Apparatus as defined in claim 15, said containers being arranged in each case in a plurality of columns substantially perpendicular to said roller axes;

said second roller comprising a plurality of roller sections individually insulated from each other and equal in number to the number of said columns and being positioned to simultaneously underlie said columns on passage of a case thereover;

a plurality of said receivers connected one to each of said roller sections; and comparator means connected to said receivers and comparing output signals thereof and providing a rejection signal when said output signals exceed a predetermined dissimilarity.

17. Apparatus as defined in claim 16, and means summing the outputs of said receivers and comparing the summed outputs thereof with said RF potential to provide the first-named rejection signal.

18. Apparatus as defined in claim 17, a plurality of differential summing amplifiers equal in number to the number of said receivers and having inputs connected to said receivers to provide the algebraic sum of the outputs of each combination of pairs of receivers;

a gate connected to said summing amplifiers; and gate signaling means connected to said gate and mounted for energizing upon movement of a case into position on said rollers.

19. Apparatus as defined in claim 18:

the fourth roller in spaced relation to one of said first and second rollers and for movement thereover of a case bottom and being spaced from said one roller to simultaneously engage each case bottom, said fourth roller being formed to provide an electrically insulated contact with said case bottoms and being connected to said RF generator;

an additional receiver connected to said fourth roller and deriving an additional electrical potential therefrom;

a comparator circuit connected to said generator and additional receiver and responsive to a predetermined difference in potential therefrom to provide a rejection signal;

an additional gate connected to said comparator circuit; and additional gate signaling means connected to said additional gate and mounted for energizing upon movement of a case into position on said first/second and fourth roller.

20. Apparatus as defined in claim 19, said lastnamed gate signaling means being mounted to provide a signal to its connected gate in a position of said case different from the case position energizing said firstnamed gate signaling means.

21. Apparatus for detecting the presence and condition of objects arranged in substantially parallel rows on or proximate to one side of a wall comprising:

means mounted at the opposite side of said wall and transmitting energy thereto;

said energy and wall providing for transmission of energy through said wall to said objects, and said energy and objects providing for return energy transmission through said wall;

means receiving said return energy from a plurality of wall areas, said wall areas being arranged in rows conforming to said rows of objects, and each of said areas being associated with one of said objects;

comparator means connected to said return energy receiving means and comparing energy quantities received from said areas;

means connected to said comparator means and responsive to a predetermined dissimilarity between said received energy quantities to provide a rejection signal;

said energy transmitting means comprising electric AC voltage generators connected to alternate rows of said wall areas; and said receiving means comprising an electrical AC sensing means connected to a row of said wall areas intermediate said rows connected to said generators.

* * * * *